(12) United States Patent
Zhou

(10) Patent No.: US 8,460,900 B2
(45) Date of Patent: Jun. 11, 2013

(54) METHODS TO DEGRADE SLUDGE FROM PULP AND PAPER MANUFACTURING

(75) Inventor: Xiangdong Zhou, Memphis, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 28 days.

(21) Appl. No.: 13/152,384

(22) Filed: Jun. 3, 2011

(65) Prior Publication Data

US 2011/0300587 A1 Dec. 8, 2011

Related U.S. Application Data

(60) Provisional application No. 61/352,526, filed on Jun. 8, 2010.

(51) Int. Cl.
*C12P 19/00* (2006.01)
*C12P 19/02* (2006.01)
*C12P 19/04* (2006.01)
*C12P 7/10* (2006.01)
*C02F 3/00* (2006.01)

(52) U.S. Cl.
USPC .......................................... 435/101; 435/262

(58) Field of Classification Search
USPC ................................. 435/101, 262
See application file for complete search history.

(56) References Cited

U.S. PATENT DOCUMENTS

| | | | |
|---|---|---|---|
| 5,324,432 A | 6/1994 | Robertson et al. | |
| 5,356,800 A | 10/1994 | Jaquess | |
| 5,395,530 A | 3/1995 | Robertson et al. | |
| 5,470,480 A | 11/1995 | Gray et al. | |
| 5,498,766 A | 3/1996 | Stuart et al. | |
| 5,507,952 A | 4/1996 | Jaquess et al. | |
| 5,514,277 A | 5/1996 | Khudenko | |
| 5,536,410 A | 7/1996 | Kitatsuji et al. | |
| 5,620,565 A * | 4/1997 | Lazorisak et al. | 162/72 |
| 5,780,283 A | 7/1998 | Lee | |
| 5,807,464 A | 9/1998 | Jobbins et al. | |
| 5,846,425 A | 12/1998 | Whiteman | |
| 6,066,233 A | 5/2000 | Olsen et al. | |
| 6,325,934 B1 | 12/2001 | Tobey, Jr. et al. | |
| 6,548,556 B2 | 4/2003 | Hobson et al. | |
| 6,610,172 B1 | 8/2003 | Lund et al. | |
| 6,946,073 B2 | 9/2005 | Daigger et al. | |
| 7,101,482 B2 | 9/2006 | Chauzy et al. | |
| 7,125,471 B2 | 10/2006 | Hill, Jr. et al. | |
| 7,344,648 B2 | 3/2008 | Cerea | |
| 7,455,997 B2 | 11/2008 | Hughes | |
| 7,582,444 B2 | 9/2009 | Hughes | |
| 7,674,379 B2 | 3/2010 | Vanotti et al. | |
| 2004/0055715 A1 | 3/2004 | Phipps | |
| 2006/0086659 A1 | 4/2006 | Szwajcer Dey et al. | |
| 2008/0190845 A1 | 8/2008 | DeLozier et al. | |
| 2008/0251374 A1 | 10/2008 | McManigal | |
| 2009/0286295 A1 | 11/2009 | Medoff et al. | |
| 2010/0055747 A1 | 3/2010 | Kelemen et al. | |
| 2010/0078307 A1 | 4/2010 | Dale et al. | |

FOREIGN PATENT DOCUMENTS

| | | |
|---|---|---|
| JP | 50020559 A | 3/1975 |
| WO | 03/048454 A2 | 6/2003 |
| WO | 2004-024640 A1 | 3/2004 |
| WO | 2009-105236 A1 | 8/2009 |

OTHER PUBLICATIONS

Kim et al. "Enhancement of the enzymatic digestibility of waste newspaper using Tween." Applied Biochemistry and Biotechnology, vol. 129-132, 2006.*
Tabka et al. "Enzymatic saccharification of wheat straw for bioethanol production by a combined cellulase xylanase and feruloyl esterase treatment." Enzyme and Microbial Technology, 39: 897-902, 2006.*
SIGMA-ALDRICH®, TWEEN® 80 product information sheet, May 2006.*
ICI Americas Inc., "The HLB System a time-saving guide to emulsifier selection." 1980.*
Rhodia, ANTEROX® 724/P product data sheet, Mar. 2010.*
Rhodia, ANTEROX® Product results, Accessed online Jul. 10, 2012 at http://www.rhodia.com.cn/en/markets_and_products/product_finder/product_results.tcm?Brand=antarox®&itemsPerPage=30.*
Shandong Longda Bio-Products Co., Ltd., Cellulase product details, Accessed online Jul. 9, 2012 at http://longda-enzyme.en.alibaba.com/product/219302259-201625347/cellulase.html.*
Shah et al., "Isolation and characterization of poly(3-hydroxybutyrate-co-3-hydroxyvalerate) degrading bacteria and purification of PHBV depolymerase from newly isolated *Bacillus* sp AF3," International Biodeterioration and Biodegradation, vol. 60, No. 2, Jul. 2007, pp. 109-115 (Abstract only—1 page).
Kannan et al., "Enzymology of Ligno-Cellulose Degradation by Pleurotus-Sajor-Caju During Growth on Paper-Mill Sludge," Biological Wastes, vol. 33, No. 1, 1990, pp. 1-8 (Abstract only—1 page).
Maki et al., "The prospects of cellulase-producing bacteria for the bioconversion of lignocellulosic biomass," International Journal of Biological Sciences, vol. 5, 2009, pp. 500-516 (22 pages).
Li et al., "Interactions between 12-EOx-12 gemini surfactants and pluronic ABA block copolymers (F108 and P103) studied by isothermal titration calorimetry," Langmuir, vol. 20, No. 3, Feb. 3, 2004, pp. 579-586 (Abstract only—1 page).
Pei et al., "Effect of protease and cellulase on the characteristic of activated sludge," J. Hazard. Mater., vol. 178, No. 1-3 Jun. 15, 2010, pp. 397-403 (Abstract only—1 page).
Fan et al., "Conversion of paper sludge to ethanol in a semicontinuous solids-fed reactor," Bioprocess Biosyst Eng., vol. 26, 2003, pp. 93-101 (Abstract only—1 page).
Shi et al., "The stimulatory effects of surfactants on composting of waste rich in cellulose," World Journal of Microbiology and Biotechnology, vol. 22, No. 11, 2006 (7 pages).
Mukhopadhyay, "Bioconversion of Paper Mill Lignocellulosic Materials to Lactic Acid Using Cellulase Enzyme Complex and Microbial Cultures," (a Thesis), Kansas State University, 2009 (60 pages).
Duff et al., "Effect of surfactant and particle size reduction on hydrolysis of deinking sludge and nonrecyclable newsprint," Biotechnology and Bioengineering, vol. 45, Issue 3, published online Feb. 19, 2004, pp. 239-244 (Abstract only—1 page).

(Continued)

*Primary Examiner* — Karen Cochrane Carlson
*Assistant Examiner* — Jennifer M. H. Tichy
(74) *Attorney, Agent, or Firm* — Kilyk & Bowersox, P.L.L.C.

(57) ABSTRACT

A method to degrade or digest sludge, such as from pulp and/or paper manufacturing, is described. Compositions to use in the method are further described.

24 Claims, No Drawings

OTHER PUBLICATIONS

Tago et al., "Exocellular Mucopolysaccharide Closely Related to Bacterial Floc Formation," Applied and Environmental Microbiology, vol. 34, No. 3, Sep. 1977 pp. 308-314 (7 pages).

Environmental Leverage, Inc., "Bioaugmentation Products, MicroSolv 118 for Pulp and Papermills," from http://www.environmentalleverage.com/microsolv118.htm (3 pages).

The International Search Report and the Written Opinion of the International Searching Authority received in corresponding International Patent Application No. PCT/US2011/039000 dated Feb. 29, 2012 (8 pages).

* cited by examiner

METHODS TO DEGRADE SLUDGE FROM PULP AND PAPER MANUFACTURING

This application claims the benefit under 35 U.S.C. §119 (e) of prior U.S. Provisional Patent Application No. 61/352,526, filed Jun. 8, 2010, which is incorporated in its entirety by reference herein.

BACKGROUND OF THE INVENTION

The present invention relates to methods to degrade biomass or sludge. The present invention further relates to compositions used to degrade biomass or sludge.

The manufacture of paper involves blending, in water, a pulp material (generally wood fiber) with fillers, such as clay, and other additives to create a stock slurry mixture referred to herein as a pulp. The pulp is then processed through a papermaking machine to form a sheet. The water is then extracted from the sheet and the sheet is then pressed and dried, thereby forming a paper product. The drained water contains an amount of fiber and filler material. This material is collected for later processing, however, the recovery is usually not complete. Discarded material and material not captured for reuse are generally transported to a waste treatment facility where still-remaining solids, e.g., the fibers and filler materials, are removed. The cleaned water is discharged back into the environment or communicated back to the papermaking process for reuse. After dewatering, the solids are contained in a concentrated, typically 40%-60% solids, papermaking sludge. The main components of this sludge are fibers and clay filler material. This sludge is usually disposed of by burying in landfills, landspreading, or incinerating. Some papermaking processes recycle papermaking sludge, however, this has been found to adversely affect sizing and cause size reversion.

The problem with burying the sludge in landfills is that this creates, in some localities, environmental issues. Further, the cost of hauling away the sludge can be quite expensive. In addition, the sludge, if not treated properly, can create odor problems in the vicinity where the sludge is located and shipped to.

Besides sludge from paper and pulp manufacturing, biomass created from various processes (for instance, plant biomass, animal biomass, and municipal waste biomass) have similar problems.

While there have been attempts to treat the sludge or biomass using various compositions and processing techniques, there is still a need in the industry to provide processes that work more predictably, cheaply, and/or at a faster rate than current techniques.

SUMMARY OF THE PRESENT INVENTION

A feature of the present invention is to provide a method to degrade sludge, for instance, from pulp and/or paper manufacturing.

A further feature of the present invention is to provide a composition that can be applied to the sludge to degrade the sludge.

A further feature of the present invention is to provide a method to treat or degrade biomass.

A further feature of the present invention is to provide a method that will break down or degrade the biomass or sludge in order to reduce the solids content.

A further feature of the present invention is to provide a method that will break down or degrade sludge to reduce the solids content and provide a liquid or slurry that can be processed in order to utilize the by-products from the degradation of the sludge or biomass, such as a fermentation process, to make bio-ethanol.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method to degrade sludge from pulp and/or paper manufacturing and/or other sources (residential and/or industrial). The method includes applying to the sludge at least one enzyme having cellulase activity and at least one non-ionic surfactant that is a difunctional block copolymer having an HLB value of at least 7. The enzyme and non-ionic surfactant can be added separately or it can be added as a pre-formed composition. The method further includes de-watering the sludge.

The present invention further relates to a composition that contains at least one enzyme having cellulase activity and at least one non-ionic surfactant that is a difunctional block copolymer having an HLB value of at least 7. The non-ionic surfactant preferably potentiates or has some synergistic interaction with the enzyme in order to increase the overall activity of the enzyme. Put another way, the use of the composition of the present invention has the ability to increase sludge solid reduction, for instance, by at least 10% greater by weight sludge reduction, than using the enzyme alone without any surfactant present.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates, in part, to a method to degrade sludge from pulp and/or paper manufacturing and/or other sources (whether residential and/or commercial or industrial). The method involves applying at least one enzyme having cellulase activity and at least one non-ionic surfactant that is a difunctional block copolymer having an HLB value of at least 7 to the sludge and/or other source(s). The enzyme and non-ionic surfactant can be added separately or as a pre-formed composition. The method further involves de-watering the sludge. As a result of this method, the sludge can be degraded such that the sludge solid content is reduced. For purposes of the present invention, the degrading of the sludge as used herein includes digesting of the sludge. By reducing the sludge solid content, the amount of sludge that needs to be disposed to a landfill or otherwise processed can be significantly reduced, if not eliminated. This provides cost savings and provides an environmentally friendly solution to the company or person in possession of the sludge.

The present invention includes the following aspects/embodiments/features in any order and/or in any combination.

1. A method to degrade sludge from pulp and/or paper manufacturing, wherein said method comprises:
   a) applying to said sludge
      i) at least one enzyme having cellulase activity, and
      ii) at least one non-ionic surfactant that is a difunctional block copolymer having an HLB value of at least 7, or a composition comprising i) and ii); and
   b) de-watering said sludge.

2. The method of any preceding or following embodiment/feature/aspect, wherein said enzyme or said composition has a cellulase activity of at least 10 units/g.

3. The method of any preceding or following embodiment/feature/aspect, wherein said non-ionic surfactant is present in an amount of at least 0.1% by weight of said i) and ii) or said composition.

4. The method of any preceding or following embodiment/feature/aspect, wherein said enzyme and said non-ionic surfactant are present in a weight ratio of enzyme:non-ionic surfactant of 0.1:10 to 10:0.1.

5. The method of any preceding or following embodiment/feature/aspect, wherein said cellulase activity of i) and ii) or said composition is at least 10% greater than using i) alone.

6. The method of any preceding or following embodiment/feature/aspect, wherein sludge solid reduction as a result of said method using i) and ii) or said composition is at least 10% greater by weight than using i) alone.

7. The method of any preceding or following embodiment/feature/aspect, wherein said enzyme comprises a lipase.

8. The method of any preceding or following embodiment/feature/aspect, wherein in said method to degrade, cellulose fiber is present in said sludge and is at least partially degraded, and wherein the solid contents of said sludge is reduced.

9. The method of any preceding or following embodiment/feature/aspect, wherein the degrading of the sludge in part forms sugar.

10. The method of any preceding or following embodiment/feature/aspect, wherein said method further comprises converting said sugar to ethanol in a fermentation process.

11. The method of any preceding or following embodiment/feature/aspect, wherein said method occurs at a temperature of from about 5° C. to about 75° C.

12. The method of any preceding or following embodiment/feature/aspect, wherein said method is conducted in the absence of any separate addition of acid or alkaline, or both.

13. The method of any preceding or following embodiment/feature/aspect, wherein said sludge comprises cellulose material.

14. The method of any preceding or following embodiment/feature/aspect, wherein said cellulose material is present in an amount of from about 0.1 wt % to about 70 wt %, based on the weight of dry sludge.

15. The method of any preceding or following embodiment/feature/aspect, wherein said non-ionic surfactant is a block copolymer of the type PEO-PPO-PEO.

16. The method of any preceding or following embodiment/feature/aspect, wherein said HLB value is at least 12.

17. The method of any preceding or following embodiment/feature/aspect, wherein said HLB value is at least 20.

18. The method of any preceding or following embodiment/feature/aspect, wherein said HLB value is at least 24 to 30.

19. The method of any preceding or following embodiment/feature/aspect, wherein said sludge is reduced to at least partially formed sugar, glucose, shorter-chain cellulose, or any combination thereof.

20. The method of any preceding or following embodiment/feature/aspect, wherein said sludge is primary sludge.

21. The method of any preceding or following embodiment/feature/aspect, wherein said sludge is secondary sludge.

22. The method of any preceding or following embodiment/feature/aspect, wherein said method prior to said de-watering said sludge occurs for a time of from about 1 hour to 120 hours.

23. The method of any preceding or following embodiment/feature/aspect, wherein said enzyme is present in a concentration of 0.05 to 35% by weight of said i) and ii), or said composition.

24. The method of any preceding or following embodiment/feature/aspect, wherein said i) and ii) are added sequentially within 30 minutes of each other in any order.

25. The method of any preceding or following embodiment/feature/aspect, where said non-ionic surfactant has an average molecular weight of from about 1,000 to about 20,000.

The present invention can include any combination of these various features or embodiments described above and/or below as set forth in sentences and/or paragraphs.

In more detail, the sludge, as stated, can be from pulp and/or paper manufacturing and/or other sources. There is no limitation as to the source of the sludge. The present invention is preferably used to degrade sludge from paper and/or paper manufacturing. Furthermore, the present invention has utility with respect to degrading biomass in general. The term "biomass" includes any non-fossilized, i.e., renewable, organic matter. The various types of biomass include plant biomass, microbial biomass, animal biomass (any animal by-product, animal waste, etc.) and municipal waste biomass (residential and light commercial refuse with recyclables such as metal and glass removed). The term biomass also includes virgin or post consumer cellulosic materials, such as rags and towels fabricated from cotton or a cotton blend.

The term "plant biomass" and "lignocellulosic biomass" refer to virtually any plant-derived organic matter (woody or non-woody). Plant biomass can include, but is not limited to, agricultural or food crops (e.g., sugarcane, sugar beets or corn kernels) or an extract therefrom (e.g., sugar from sugarcane and corn starch from corn), agricultural crops and agricultural crop wastes and residues such as corn stover, wheat straw, rice straw, sugar cane bagasse, cotton and the like. Plant biomass further includes, but is not limited to, trees, woody energy crops, wood wastes and residues such as softwood forest thinnings, barky wastes, sawdust, paper and pulp industry waste streams, wood fiber, and the like. Additionally, grass crops, such as switchgrass and the like have potential to be produced on a large-scale as another plant biomass source. For urban areas, the best potential plant biomass feedstock includes yard waste (e.g., grass clippings, leaves, tree clippings, and brush) and vegetable processing waste.

It is to be understood that while various descriptions of the present invention are provided with respect to sludge, especially sludge from pulp and/or paper manufacturing, the present invention also applies to all forms of sludge and/or biomass in the same or similar manner.

The sludge to be treated by the present invention can be a primary and/or secondary sludge as those terms are understood in the papermaking industry. The sludge can include, but is not limited to, compositions containing one or more types of fibers of one or more wood types. The sludge can contain fibers of one or more lengths, including fines. Other materials can be included in the papermaking sludge, which can include, but not are not limited to, ASA sizing materials or other sizing materials, hydrolyzed sizing materials, polymers, stickies, glues, inks, fillers, other impurities, such as from recycled paper, de-foamers, and the like.

With respect to the enzyme having cellulase activity, one or more enzymes having cellulase activity can be used, such as 2 or more enzymes, 3 or more enzymes, 4 or more enzymes, 5 or more enzymes, and the like. Other enzymes that do not have cellulase activity can be further included as an option.

The enzyme composition can contain at least one esterase or lipase, or both, and preferably contains a high concentration of esterase and/or lipase. The lipase can be derived or isolated from pancreatic sources (e.g., pancreatic lipase) or from various fungi and/or bacteria, and/or other microorganisms. Examples include, but are not limited to, triacylglycerol acylhydrolase, and triacyl glycerol lipase. Also, any lipase or esterase capable of hydrolyzing triglycerides to glycerol and fatty acids can be used. Commercially available products containing esterase or lipase can be used. For instance, BUZYME® 2515 and BUZYME® 2517 can be used and are available from Buckman Laboratories International, Inc., Memphis, Tenn. Products containing suitable enzymes, such as RESINASE® A2X, NOVOCOR® ADL, Pancreatic Lipase 250, Lipase G-1000, GREASEX® 50L, and GREASEX® 100L, can be used in the methods of the present invention. Such products are available from such commercial sources as GENENCOR® and NOVO NORDISK®. The esterase or lipase described in U.S. Pat. Nos. 5,507,952 and 5,356,800 can be used in the present invention and these patents are incorporated in their entirety along with any other patents or publications mentioned in this application, by reference herein. The enzyme or lipase can generally be used in any form, such as liquid form or solid form. Amounts of esterase and/or lipase can be from about 0.005 lbs. to about 4.0 lbs. per ton of sludge based on the dried solids weight of the sludge, such as from about 0.01 pound to about 2.0 pounds per ton, or from about 0.05 pound to about 0.5 pound per ton of sludge based on the dried solids weight of the sludge. The esterase and lipase compositions can be stabilized compositions, such as using the formulations described in U.S. Pat. Nos. 5,356,800 and 5,780,283, which are incorporated herein in their entireties by reference.

According to the present invention, the enzyme composition can include a combination of two or more different enzymes. The enzyme composition can include, for example, a combination of a lipase and a cellulase, and optionally can include a stabilizing agent. The stabilizing agent may be a polyamide oligomer.

Preferably, though not required, the enzyme or the composition containing the enzyme (e.g., a pre-formed composition containing the enzyme and non-ionic surfactant of the present invention) can have a cellulase activity of at least 10 units/g. For instance, the enzyme or the composition containing the enzyme can have a cellulase activity of at least 15 units/g, at least 20 units/g, at least 25 units/g, at least 100 units/g, at least 500 units/g, for instance, from 10 units/g to 1,500 units/g or higher.

The enzyme can be present in any concentration amount as long as the enzyme or enzyme containing composition has the ability to degrade the sludge. For instance, the enzyme can be present in a concentration of about 0.05 to about 5% by weight, based on the weight of the enzyme and non-ionic surfactant present. For example, the concentration of the enzyme can be from 0.1 wt % to 35 wt %, from 0.5 wt % to 35 wt %, from 1 wt % to 35 wt % or more, from 2 wt % to 35 wt %, from 5 wt % to 35 wt %, from 10 wt % to 35 wt %, from 15 wt % to 35 wt %, from 20 wt % to 35 wt % or more, all based on the total weight of the enzyme and non-ionic surfactant present.

With regard to the non-ionic surfactant, at least one non-ionic surfactant that is a difunctional block copolymer having an HLB value of at least 7 is used. For example, the HLB value can be at least 10, at least 12, at least 14, at least 18, at least 20, at least 24, at least 25. For instance, the HLB value can be from 7 to 30, from 10 to 30, from 10 to 28, from 10 to 25, from 10 to 24, from 12 to 30, from 12 to 25, from 12 to 24, from 15 to 24, from 15 to 30, from 20 to 30, and the like. At least one non-ionic surfactant that is a difunctional block copolymer can be used, or 2 or more, 3 or more, and the like. The non-ionic surfactant is present, preferably in an amount of at least 0.1% by weight based on the weight of the enzyme and non-ionic surfactant present. Other non-ionic surfactants that have an HLB value below 7 and/or are not difunctional block copolymers can be used in addition as an option. As a further option, other surfactants can be present as long as the overall composition containing the enzyme and non-ionic surfactant are not effected with regard to their ability to degrade sludge as described herein.

The non-ionic surfactant can be a block copolymer of the type PEO-PPO-PEO. The non-ionic surfactant can be a poloxamer. For instance, the non-ionic surfactant that can be used in the present invention can have the following formula:

These are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol. These polymers are also well known by the trade name PLURONICS™. These compounds are commonly named with the word Poloxamer followed by a number to indicate the specific co-polymer, for example Poloxamer 407 having two PEG blocks of about 101 units ($y^1$ and $y^3$ each equal to 101) and a polypropylene block of about 56 units. This polymer is available from BASF under the trade name LUTROL™ F-17.

Some other specific examples include, polyethylene glycol, including ester derivatives thereof, such as its methyl ester or the esters of fatty acids (e.g., PEG-palmitate). Block polymers of the type PEO-PPO-PEO, and random PEO-PPO polymers can be used. Further, TRITON® X-100 (polyethylene glycol p-(1,1,3,3-tetramethylbutyl)-phenyl ether), which is non-ionic surfactant that comprises a polyethylene glycol moiety, can be used.

The enzyme and non-ionic surfactant that is a difunctional block copolymer can be present in a weight ratio of enzyme: non-ionic surfactant of 0.1:10 to 10:0.1. Preferably, the weight ratio is from 1:0.5, such as 1:5, and the like.

The non-ionic surfactant can have an average molecular weight (in Daltons) of from 1,000 to about 20,000, for instance, 2,000 to 15,000, 3,000 to 12,000, 5,000 to 20,000, 10,000 to 20,000, and the like.

Besides the enzyme and non-ionic surfactant, other components can be used in addition, such as preservatives, stabilizing agents, deodorants, fillers, extenders, and the like. For instance, besides the enzyme and non-ionic surfactant, at least one stabilizer can be used, such as a PVP with or without glycerol. Further, one or more salts can be present, such as calcium chloride or other salts. The enzyme and non-ionic surfactant can be diluted or prepared in water or other aqueous solutions. For instance, the glycerol or similar component can be present in an amount of 5 to 30% by weight of composition. The PVP, such as PVP K90 or similar component, can be present in an amount of from about 1 to 10 wt %. The $CaCl_2$ or similar component can be present in an amount of from about 0.1 to 2 wt %. The preservative, such as BUSAN 1078, can be present in an amount of from 0.05 wt % to about 0.2 wt %, wherein all weight percents are based on the total weight of composition (without dilution with water).

Besides these components, biocides, preferably in small amounts simply to preserve the composition of the present invention for storage purposes, can be used, such as biocides from Buckman Laboratories International, such as BUSAN® 1078, and the like.

If biocides are present, typically, the amounts are below 1% by weight based on the overall weight of the components present that form the composition of the present invention. More preferably, less than 0.5 wt %, less than 0.1 wt %, such as 0.001 wt % to 0.01 wt % by weight of the overall composition.

As stated, in the present invention, the enzyme, non-ionic surfactant, and any optional components can be added together as a pre-formed composition or each individual component or any combination of components can be added separately, such as sequentially, batchwise, or at the same time through different inlet injection points. The composition or components thereof can be introduced incrementally over any time period (10 seconds to 150 hours or more), or can be introduced periodically or all at one time. As an option, a pre-formed composition can be made, which contains the enzyme and non-ionic surfactant and other components. The composition can be prepared by mixing the components together in any order. The various amounts of the enzyme and non-ionic surfactant are described above and apply equally here. Generally, water or an aqueous component or solution is used to form the composition. The water or aqueous solution or component can be present in an amount of from about 10 wt % to about 90 wt %, based on the total weight of the composition diluted with water.

The composition of the present invention or the components that form the composition of the present invention can be applied or introduced to the sludge in any manner, such as by spraying, pouring, injecting, mixing in, and the like. Essentially, any contact technique to bring the components of the composition of the present invention into contact with the sludge can be used. The composition of the present invention or the components that make up the composition can be subsequently mixed with the sludge or otherwise dispersed amongst the sludge in order to improve the degradation rate. As an option, the composition can be in liquid form, solid form, dry form, tablet form, or semi-solid form. The composition can be incorporated or present in a cartridge, or can be present in a membrane or filter or on any surface that contacts the sludge.

The composition of the present invention or components that make up the composition can be introduced to the sludge that is present in a tank, in a settling pond, and/or other containment location. Preferably, the present invention is generally used with un-activated sludge. The water content of the sludge that is being treated can be any water content, such as from about 1 to about 99 wt %. The sludge can be de-watered sludge, can be primary sludge, such as sludge existing before any aerobic processing and/or can be after primary oxidative processing, which is a secondary sludge.

Generally, the sludge that is being treated contains cellulose material, such as from about 0.1 wt % to about 70 wt % cellulose material based on the weight of the dry sludge.

With the present invention, the sludge can be reduced to components that include sugar, glucose, celluloses, such as shorter chain celluloses and the like.

The method of the present invention can occur at various temperatures, such as ambient temperatures (referring to the temperature of the sludge). The method the present invention can be used, for instance, at temperatures of from about 5° C. to about 75° C.

With the present invention, as an option, the method is conducted in the absence of any separate addition of acid and/or alkaline component or chemical.

With the present invention, after the enzyme and non-ionic surfactant are brought into contact with the sludge, the contact time can be from about 1 hour to about 150 hours or more. For instance, the contact time can be from 5 hours to 100 hours, 10 hours to 75 hours, 24 hours to 72 hours, 48 hours or more, and the like. There is no true time limitation for the contact time. Generally, contact time can be based on the particular process used at the location of the sludge. After this contact time, the de-watering of the sludge can occur. Any method to de-water sludge can be used that is known in the art. For instance, the de-watering can be achieved with use of a settling tank or pond and then pressing, extruding, filtering, centrifuging, and the like. There is no limitation with regard to the technique or techniques that can be used to de-water the sludge.

If the non-ionic surfactant and enzyme are added separately and not as a pre-formed composition, preferably the non-ionic surfactant and enzyme are added within 30 minutes of each other in any order, within 15 minutes of each other in any order, within 10 minutes of each other in any order, within 5 minutes of each other in any order, within 1 minute of each other in any order, or within 30 seconds of each other in any order.

Any subsequent processing of the de-watered (and degraded) sludge (e.g., any remaining sludge) can be used and there are no limitations with respect to the further processing. As stated, with the method of the present invention, the sludge that is degraded can be reduced by 10% by weight, 20% by weight, 30% by weight, 40% by weight, 50% by weight, or more. The sludge that can exist after the method of the present invention is conducted can then be processed per conventional techniques. The products or by-products of the degraded sludge can be, for instance, in the form of sugar, glucose, shorter chain cellulose, and the like, and can generally be present in the form of a slurry or in solution and this material can then be recovered for any purposes, such as for fermentation to make bio-ethanol. As an alternative, the solution or slurry containing the degraded products of the methods of the present invention can be put back into the system, such as liquid in an aerobic tank. In the alternative, the solution or slurry containing the products of the degradation of the sludge can be processed as BOD material.

With the present invention, the cellulase activity of the enzyme is greatly increased by the presence of the non-ionic surfactant. For instance, the cellulase activity of the enzyme is increased by at least 10% compared to just using the enzyme alone without any non-ionic surfactant present. This increased activity can be at least 10% greater, at least 20% greater, at least 25% greater, at least 30% greater, at least 35% greater or more, such as from 10% to 50% greater in cellulase activity.

With the present invention, the solids reduction of the sludge, as a result of the methods of the present invention, can be increased by at least 10% (by weight) as compared to using enzyme alone without any non-ionic surfactant being present. This solids reduction can be at least 10 wt % greater, at least 15 wt % greater, at least 20 wt % greater, at least 25 wt % greater, at least 30 wt % greater, such as from 10 wt % to 50 wt % greater (compared to no non-ionic surfactant present).

As an option, in the present invention, though less effective, the non-ionic surfactant, in at least one embodiment, can be optional.

The present invention will be further clarified by the following examples, which are intended to be exemplary of the present invention.

EXAMPLES

Example 1

Sludge obtained from a paper manufacturing plant was obtained. This sludge had a consistency of 56.0% by weight sludge in water. The sludge was diluted in de-ionized water to contain 9.1 wt % solid. The solid sludge suspension had a pH of about 6.95.

Two compositions were prepared. The first composition contained enzyme in various amounts shown in the table below. Particularly, the first set of compositions contained enzyme only, specifically CELLIC® CTec enzyme from NOVOZYMES®. The second set of compositions contained the same enzyme but, in addition, a non-ionic surfactant, specifically PLURONIC F108 from BASF. The amounts for each component are set forth in the table below. The treatment with either composition was conducted at 28° C. for 24 hours. The sludge suspension was vigorously vortexed for 2 to 3 minutes to de-integrate the tight pack sludge before enzyme addition.

As can be seen from the results below, when the enzyme with non-ionic surfactant was used, the amount of sludge solid reduction increased in each instance compared to using enzyme alone.

TABLE 1

Sludge digestion (28° C., pH 6.95 for 24 hours)

| Treatment (wt %) (24 hr at pH 6.95) | Sludge dry weight (g) (before treatment) | Sludge dry weight (g) (after treatment) | Sludge solid reduction (%) |
|---|---|---|---|
| CTec - 0.05%* | 1.82 | 1.6617 | 8.7 |
| CTec - 0.1% | 1.82 | 1.6143 | 11.3 |
| CTec - 0.5% | 1.82 | 1.4433 | 20.7 |
| CTec - 1.0% | 1.82 | 1.0774 | 40.8 |
| CTec - 10% | 1.82 | 0.8882 | 51.2 |
| CTec - 0.05% + 10% F108 | 1.82 | 1.6289 | 10.5 |
| CTec - 0.1% + 10% F108 | 1.82 | 1.5161 | 16.7 |
| CTec - 0.5% + 10% F108 | 1.82 | 1.2594 | 30.8 |
| CTec - 1.0% + 10% F108 | 1.82 | 1.0265 | 43.6 |
| CTec - 10% + 10% F108 | 1.82 | 0.8609 | 52.7 |
| Control (no enzyme) | 1.82 | 1.7618 | 3.2 |

*The enzyme concentrations are based on percent of sludge suspension.

Example 2

The experiments were set up for evaluating the effects of surfactants on enzymatic activity of CELLIC® CTec enzyme. The enzyme, surfactant, and water were mixed to form a solution containing 5 wt % surfactant and 10 wt % enzyme. For example, 1.0 g of CELLIC® CTec, 0.5 g of PLURONIC F108, and 8.5 g of deionized water were mixed to produce a solution containing 10 wt % enzyme and 5 wt % surfactant. The resulted enzyme-surfactant solutions were tested for cellulase activity. Carboxymethyl cellulose was used as the assay substrate. A control solution containing 10 wt % enzyme without surfactant was included for comparison.

1. Effects of Various PLURONIC Surfactants on the Activity of CELLIC® CTec

Five PLURONIC surfactants with different HLB values are evaluated for their effects on the enzymatic activity of CELLIC® CTec in water solution. Each surfactant was mixed with the enzyme in water. The resulting solution was then assayed for cellulase activity using carboxymethyl cellulose (CMC) as the substrate. The results are shown in the Table below. All five PLURONIC surfactants demonstrated positive effects on the enzyme activity. F108 was the best among the tested PLURONIC surfactants. F108 enhanced the enzymatic activity by 22.3%. All five PLURONIC surfactants showed no enzyme activity when tested alone without the enzyme.

TABLE 2

Effects of surfactants on enzymatic activity
(Test system: 5 wt % PLURONIC ®
surfactant + 10 wt % CELLIC ® CTec)

| Surfactant | HLB | Cellulase Activity (u/g) | % Activity Increase |
|---|---|---|---|
| Pluronic ® F108 | >24 | 412.2 | 22.3 |
| Pluronic ® F127 | 18-23 | 374.2 | 11.0 |
| Pluronic ® P85 | 12-18 | 368.7 | 9.4 |
| Pluronic ® P123 | 7-12 | 372.3 | 10.5 |
| Pluronic ® 25R2 | 1-7 | 358.2 | 6.3 |
| Control | — | 337.0 | — |

Control - 10% CELLIC ® CTec solution without surfactant.
HLB - hydrophilic lipophilic balance.

2. Effects of Other Surfactants (Other than PLURONIC®) on CELLIC® CTec Activity

TABLE 3

Effects of other surfactants on enzymatic activity
(Test system: 5 wt % surfactant + 10 wt % CELLIC ® CTec)

| Surfactant | Cellulase Activity (u/g) | % Activity Increase |
|---|---|---|
| Castor oil ethoxylate, non-ionic | 335.6 | 2.0 |
| Tallow amine ethoxylate, cationic | 346.3 | 5.3 |
| Cocobis(2-hydroxyethyl)methyl ammonium chloride, cationic | 351.6 | 6.9 |
| Sorbitan mono-oleate ester, non-ionic | 353.1 | 7.3 |
| Sorbitan mono-oleate, non-ionic | 321.5 | -2.3 |
| Control (no surfactant, just enzyme) | 329.0 | — |

Data in Table 3 suggest that the effect of the other tested surfactants on the enzyme activity is non-significant.

Thus, as can be seen in these examples, not all surfactants have the ability to increase the activity of the enzyme in a significant way. Further, as show in the examples, the higher the HLB value of the non-ionic surfactant, the higher percent activity increase with the enzyme. The results certainly were unexpected and surprising with regard to the effect of the non-ionic surfactant, especially a non-ionic surfactant having the HLB values of 7 or above, and more preferably, 12 or above.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method to degrade sludge from pulp and/or paper manufacturing, wherein said method comprises:
   a) applying to said sludge
      i) at least one enzyme having cellulase activity, and
      ii) at least one non-ionic surfactant that is a difunctional block copolymer having a Hydrophile-Lipophile Balance (HLB) value of at least 7, or a composition comprising i) and ii), wherein said sludge comprises cellulose material; and
   b) de-watering said sludge.

2. The method of claim 1, wherein said enzyme or said composition has a cellulase activity of at least 10 units/g.

3. The method of claim 1, wherein said non-ionic surfactant is present in an amount of at least 0.1% by weight of said i) and ii) or said composition.

4. The method of claim 1, wherein said enzyme and said non-ionic surfactant are present in a weight ratio of enzyme: non-ionic surfactant of 0.1:10 to 10:0.1.

5. The method of claim 1, wherein said cellulase activity of i) and ii) or said composition is at least 10% greater than using i) alone.

6. The method of claim 1, wherein sludge solid reduction as a result of said method using i) and ii) or said composition is at least 10% greater by weight than using i) alone.

7. The method of claim 1, wherein said enzyme further comprises a lipase.

8. The method of claim 1, wherein in said method to degrade, cellulose fiber is present in said sludge and is at least partially degraded, and wherein the solid contents of said sludge is reduced.

9. The method of claim 1, wherein degrading of the sludge in part forms sugar.

10. The method of claim 9, wherein said method further comprises converting said sugar to ethanol in a fermentation process.

11. The method of claim 1, wherein said method occurs at a temperature of from about 5° C. to about 75° C.

12. The method of claim 1, wherein said method is conducted in the absence of any separate addition of acid or alkaline, or both.

13. The method of claim 1, wherein said cellulose material is present in an amount of from about 0.1 wt % to about 70 wt %, based on the weight of dry sludge.

14. The method of claim 1, wherein said non-ionic surfactant is a block copolymer of the type PEO-PPO-PEO.

15. The method of claim 1, wherein said HLB value is at least 12.

16. The method of claim 1, wherein said HLB value is at least 20.

17. The method of claim 1, wherein said HLB value is at least 25 to 30.

18. The method of claim 1, wherein said sludge is reduced to sugar, glucose, shorter-chain cellulose, or any combination thereof.

19. The method of claim 1, wherein said sludge is primary sludge.

20. The method of claim 1, wherein said sludge is secondary sludge.

21. The method of claim 1, wherein said method prior to said de-watering said sludge occurs for a time of from about 1 hour to 120 hours.

22. The method of claim 1, wherein said enzyme is present in a concentration of 0.05 to 35% by weight of said composition.

23. The method of claim 1, wherein said i) and ii) are added sequentially within 30 minutes of each other in any order.

24. The method of claim 1, where said non-ionic surfactant has an average molecular weight of from about 1,000 to about 20,000.

* * * * *